(12) United States Patent
Kondo

(10) Patent No.: US 7,824,888 B2
(45) Date of Patent: Nov. 2, 2010

(54) METHODS FOR ASSESSING FATIGUE LEVEL AND APPLICATIONS THEREOF

(75) Inventor: Kazuhiro Kondo, Tokyo (JP)

(73) Assignee: Virus Ikagaku Kenkyusho Inc., Osaka (JP)

( * ) Notice: Subject to any disclaimer, the term of this patent is extended or adjusted under 35 U.S.C. 154(b) by 56 days.

(21) Appl. No.: 11/632,306

(22) PCT Filed: Jul. 13, 2005

(86) PCT No.: PCT/JP2005/012962

§ 371 (c)(1),
(2), (4) Date: Aug. 31, 2007

(87) PCT Pub. No.: WO2006/006634

PCT Pub. Date: Jan. 19, 2006

(65) Prior Publication Data

US 2008/0280283 A1 Nov. 13, 2008

(30) Foreign Application Priority Data

Jul. 14, 2004 (JP) .............................. 2004-235667

(51) Int. Cl.
*C12P 19/34* (2006.01)
(52) U.S. Cl. .................... 435/91.2; 435/91.33; 435/5
(58) Field of Classification Search .................. None
See application file for complete search history.

(56) References Cited

U.S. PATENT DOCUMENTS 5,985,546 A * 11/1999 Martin .......................... 435/5

FOREIGN PATENT DOCUMENTS

| JP | 11-38004 A | 2/1999 |
| JP | 11-304792 A | 11/1999 |
| JP | 11-304793 | 11/1999 |
| WO | WO 2006/006634 A1 | 1/2006 |

OTHER PUBLICATIONS

Ablashi et al, Journal of Clinical Virology, 2000, vol. 16, pp. 179-191.*
Kondo (2003) "Herpesvirus Kansen to Mansei Hiro" Igaku no Ayumi vol. 204, No. 5: 398-402.
Kurata et al. (1993) "'CFS Kanja Kesseichu EB Virus, HHV-6 Oyobi-HHV-7 no Kotai Kensaku', Koseisho Tokubetsu Kenkyu Jigyo, Honpo ni Okeru Mansei Hiro Shokogun no Jittai Chosa Narabini Byoin Byotai ni Kansuru Kenkyu" Heisei 4 Nendo Kenkyu Gyoseki Hokokusho pp. 53-54.
Kondo (Sep. 25, 2004) "Virus no Senpuku Kansen Tanpakushitsu to Hiro" Molecular Medicine vol. 41, No. 10: 1216-1221.
Kondo (May 10, 2005) "Human Herpesvirus 6 to CFS." Progress in Medicine vol. 25, No. 5: 1315-1319.
Cone, et al. (1999) "Human Herpesvirus 6 Infections after Bone Marrow Transplantation: Clinical and Virologic Manifestations." The Journal of Infectious Diseases 179: 311-318.
Yalcin, et al. (1994) "Prevalence of Human Herpesvirus 6 Variants A and B in Patients with Chronic Fatigue Syndrome." Microbiol. Immunol. 38(7): 587-590.
Gerna, et al. (May 1983) "Typing of herpes simplex virus isolates by enzyme-linked immunosorbent assay: comparison between indirect and double-antibody sandwich techniques." J. Clin Microbiol. 17(5): 942-944.
Kido, et al. (Nov. 1990) "Detection of human herpesvirus 6 DNA in throat swabs by polymerase chain reaction." Journal of Medical Virology 32(3): 139-42.
Kondo, et al. (May 1993) "Association of human herpesvirus 6 infection of the central nervous system with recurrence of febrile convulsions." Journal of Infectious Disease 167(5): 1197-200.
Kondo (2005) "Human herpesvirus latency and fatigue." Uirusu 55(1): 9-17 [English Abstract].

* cited by examiner

*Primary Examiner*—Ali R. Salimi
(74) *Attorney, Agent, or Firm*—Hunton & Williams LLP

(57) ABSTRACT

Level of fatigue that accompanies everyday life or a disease can be simply, easily, and quantitatively assessed by obtaining a body fluid from a test subject and measuring the amount of human herpesvirus in the body fluid. Furthermore, the anti-fatigue potency of anti-fatigue substances and anti-fatigue food products can be measured.

8 Claims, 3 Drawing Sheets

| DAYS | ACTIVITY OF TEST SUBJECTS |
|---|---|
| 1 (THE FIRST TEST DAY) | ORDINARY WORK |
| 2 | ORDINARY WORK (WITH A TWO-DAY HOLIDAY (IRREGULAR)) |
| 3 | |
| 4 | |
| 5 | |
| 6 | |
| 7 | |
| 8 | HOLIDAY |
| 9 | |
| 10 | |
| 11 | |
| 12 | |
| 13 | |
| 14 | |
| 15 (THE SECOND TEST DAY) | ORDINARY WORK |

FIG. 1

SEQUENCE LISTING

<160> NUMBER OF SEQ IDS NOS: 14

<210> SEQ ID NO 1
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 1
ttctccagat gtgccaggga aatcc                                              25

<210> SEQ ID NO 2
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 2
catcattgtt atcgctttca ctctc                                              25

<210> SEQ ID NO 3
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 3
agtgacagat ctgggcggcc ctaataactt                                         30

<210> SEQ ID NO 4
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 4
aggtgctgag tgatcagttt cataaccaaa                                         30

<210> SEQ ID NO 5
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 5
tggaaagaag tggagctact tcacc                                              25

<210> SEQ ID NO 6
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 6
ctgccagttt aatatccgag gaagc                                              25

<210> SEQ ID NO 7
<211> LENGTH: 27

```
<212> TYPE: DNA
<213> ORGANISM: Artificial Sequence
<220> FEATURE:
<223> OTHER INFORMATION: Chemically Synthesized

<400> SEQUENCE: 7
ccatctgaaa ccatggcatc gaatgac                                              27

<210> SEQ ID NO 8
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 8
gtggaatagg aagcatttgc cgttgc                                               26

<210> SEQ ID NO 9
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 9
atgcccagta catgacctta tggg                                                 24

<210> SEQ ID NO 10
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 10
ccagactcag ctgactgtta acctccttcc                                           30

<210> SEQ ID NO 11
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 11
taagcagagc tcgtttagtg aaccg                                                25

<210> SEQ ID NO 12
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 12
caggattatc agggtccatc tttctcttgg                                           30

<210> SEQ ID NO 13
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 13
```

```
-continued ctttagaggc gaatgggcgc ca                                              22

<210> SEQ ID NO 14
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 14
tccagggcct tcacttcggt ct                                              22
```

METHODS FOR ASSESSING FATIGUE LEVEL AND APPLICATIONS THEREOF

This application is the National Stage filing of International Application No. PCT/JP2005/012962 filed Jul. 13, 2005, which claims priority to Japanese Patent Application No. JP 2004-235667, filed Jul. 14, 2004.

TECHNICAL FIELD

The present invention relates to methods for assessing human fatigue level and methods of application thereof, kits for assessing fatigue level, and methods for measuring anti-fatigue activity of anti-fatigue substances.

BACKGROUND ART

Fatigue is a very familiar problem in everyday life. Many modern people who are under a lot of stress suffer from various kinds of fatigue. However, scientific and/or medical studies relating to "fatigue" have only been fragmentarily conducted, and hardly any studies have been done on decisive means or quantitative standards for quantitatively and objectively expressing "fatigue", which is a subjective symptom.

So far, muscle fatigue (exercise fatigue) has been mainly studied as a representative example of "fatigue". The indicator focused on in this case is an increase in the production of lactic acid in muscles. However, lactic acid is basically an important energy source for the cranial nervous system, and the theory that it inhibits muscle activity is now negatively perceived. In addition, during muscle fatigue, the phenomena of increase of pyruvic acid and drop of pH value in body fluids are known to occur. These phenomena are indeed observed when a certain stress, a load to muscle (exercise load), is given; however "fatigue" is different from local muscle exhaustion and is considered to be a broader and larger physiological phenomenon that manifests in the living body.

Patent Document 1 discloses a method for quantifying stress by using as indicators concentrations of adrenal sex steroids and their metabolites in saliva. Patent Documents 2 and 3 disclose a method for assessing the anti mental fatigue activity of test substances by measuring amino acids such as taurine, leucine, and isoleucine in blood. Although these documents disclose methods for assessing stress or fatigue by using biological factors in body fluids as indicators, the quantification of fatigue in everyday life is yet to be achieved.

Immune strength is thought to deteriorate when humans are fatigued, and virus infection can be given as one form of expression of this deterioration of human immune strength. However, a relationship between fatigue and virus infection in humans has not been elucidated.

Eight species have so far been identified as herpesviruses that mainly infect humans. Herpesviruses are large DNA viruses. They are classified into three subfamilies α, β, and γ, mainly according to the phylogenetic tree of evolution, and each subfamily has common biological characteristics. For instance, α-herpesvirus is neurotropic and undergoes latent infection and reactivation in nerve cells, and γ-herpesvirus has tumorigenicity.

Characteristics common to all herpesviruses include establishment of latent infection by viruses hiding within the body following mainly childhood infections, and recommencement of growth following some stimuli (reactivation).

Fatigue, especially mental fatigue and stress, is cited as a possible stimulus that induces reactivation. Among herpesviruses, herpes simplex virus type 1 is the causative of labial herpes. The reactivation of this virus is often observed as manifestation of labial herpes, which happens in many cases when virus carriers become extremely exhausted.

However, it actually remains almost unknown as to the sort of stimulus that induces the reactivation of herpesviruses. The relationship between the reactivation of herpesviruses and fatigue/stress has not been scientifically proven, and the above-mentioned relationship between herpes simplex virus type 1 and fatigue is merely a folk belief.

As mentioned above, methods for objectively judging muscle fatigue (exercise fatigue) due to muscle load (exercise load) have been proposed. However, hardly any reports exist regarding an objective method for assessing fatigue symptoms of everyday life although many modern people are experiencing them. Fatigue symptoms of everyday life, if they are ignored, carry the risk of directly resulting in death from overwork, a sudden death caused by long-term overworking. Although the problem of overwork death is recognized as very important from medical, economic, and social standpoints, scientific mechanisms underlying it are hardly clarified. Therefore, an objective method for assessing fatigue level is required in order to prevent overwork death, which has recently become a social problem.

Furthermore, since most medicines, health foods, or such, including nutrition-supplement drinks that are flooding the market, advertise fatigue recovery or prevention functions, scientific evidence regarding the functionality is widely required not only by consumers, but also by the market and society as a whole.

As mentioned above, knowledge on fatigue caused by exercise load is present. However, fatigue caused by exercise load and fatigue in everyday life are completely different from each other, and a method for assessing fatigue in everyday life has not been developed. Thus, the development of a simple, easy, and objective in vivo method for assessing fatigue in everyday life and their methods of application are strongly required.

[Patent Document 1]
Japanese Patent Application Kokai Publication No. (JP-A) Hei 11-038004 (unexamined, published Japanese patent application)

[Patent Document 2]
JP-A Hei 11-304792

[Patent Document 3]
JP-A Hei 11-304793

DISCLOSURE OF THE INVENTION

Problems to be Solved by the Invention

An objective of the present invention is to provide methods for simply, easily, and quantitatively assessing fatigue level, methods of application thereof, kits for assessing fatigue level, and methods for measuring anti-fatigue potency of anti-fatigue substances.

Means for Solving the Problems

As a result of dedicated investigations in view of the above problems, the present inventors made the original discovery that levels of fatigue caused in everyday life can be quantitatively assessed by measuring and assessing the amount of human herpesvirus (HHV) in a body fluid, and completed the present invention that enables the measurement of fatigue levels in everyday life by utilizing this experimental system.

Namely, the present invention's methods for assessing fatigue level are characterized by assessing fatigue levels using, as an indicator, the amount of at least one species of HHV in a body fluid, in order to solve the above problems. The above-mentioned methods can simply, easily, and objectively assess the degree of fatigue in humans, and can also quantitatively estimate an effect and efficacy of medicines having the effect of restoring or preventing fatigue, as well as that of nutritional supplement food products such as nutrition-supplement drinks or health foods. Furthermore, an overworked state, which is apt to be caused by long hours of work and such, can be simply, easily, and objectively detected.

The kits for assessing fatigue level according to the present invention are characterized by being used to carry out the above-mentioned methods for assessing fatigue level in order to solve the above-mentioned problems.

The methods for assessing anti-fatigue potency of anti-fatigue substances according to the present invention are characterized by measuring anti-fatigue potency of anti-fatigue substances with either the above-mentioned methods for assessing fatigue level or the kits for assessing fatigue level, in order to solve the above-mentioned problems.

Namely, in order to solve the above-mentioned problems, the following inventions are specifically provided:

[1] A method of assessing fatigue level, comprising assessing fatigue level of a test subject using human herpesvirus amount in a body fluid as an indicator.

[2] The method of assessing fatigue level of [1], wherein the fatigue level is assessed to be high when the amount of human herpesvirus is high.

[3] The method of assessing fatigue level of [2], wherein the amount of human herpesvirus is measured as an expression level of a gene of human herpesvirus.

[4] The method of assessing fatigue level of any one of [1] to [3], wherein the method comprises assessing the test subject to be in a state of overwork due to an accumulation of medium- or long-term acute fatigue arising from everyday life, when the amount of human herpesvirus is high.

[5] The method of assessing fatigue level of any one of [1] to [3], wherein the method comprises assessing the subject to be in a state of chronic fatigue caused by a disease when the amount of human herpesvirus is high.

[6] The method of assessing fatigue level of any one of [1] to [5], wherein the fatigue level is the level of medium- or long-term fatigue caused by everyday life or fatigue caused by a disease, and mental fatigue and/or complex fatigue.

[7] The method of assessing fatigue level of any one of [1] to [6], wherein the body fluid is at least one fluid selected from blood, saliva, cerebrospinal fluid, and urine.

[8] The method of assessing fatigue level of any one of [1] to [7], wherein the herpesvirus is at least one virus selected from human herpesvirus 6, human herpesvirus 7, human cytomegalovirus, and Epstein-Barr virus (EBV).

[9] A kit for assessing fatigue level, wherein the kit is for carrying out the method of assessing fatigue level of any one of [1] to [8].

[10] The kit of [9], comprising a means for measuring the amount of HHV in a collected body fluid, and which carries an indication that the kit can be used to assess fatigue level of a test subject using human herpesvirus amount in a body fluid as an indicator.

[11] A method of assessing an anti-fatigue effect of a candidate anti-fatigue substance, wherein the method comprises:
(i) a pre-intake HHV amount-measuring step, which comprises obtaining a body fluid from a test subject before the test subject takes the candidate anti-fatigue substance and measuring the amount of HHV in the body fluid;
(ii) a post-intake HHV amount-measuring step, which comprises obtaining a body fluid from the test subject after the test subject takes the candidate anti-fatigue substance and measuring the amount of HHV in the body fluid;
(iii) a change-in-virus-amount-calculating step, which comprises calculating a change in an HHV amount in a body fluid before and after the intake of the candidate anti-fatigue substance, based on the measurement result on a change in an HHV amount before and after the intake of the candidate anti-fatigue substance, which result is obtained through the pre-intake HIV amount-measuring step of (i) and the post-intake HHV amount-measuring step of (ii); and
(iv) an anti-fatigue potency-measuring step, which comprises measuring an in vivo anti-fatigue potency of the candidate anti-fatigue substance based on the change in the HHV amount in the body fluid before and after the intake of the candidate anti-fatigue substance, which change is obtained by the change-in-virus-amount-calculating step of (iii).

[12] A method of assessing an anti-fatigue effect of a candidate anti-fatigue substance, wherein the method comprises:
(i) an HHV amount-measuring step, which comprises obtaining a body fluid from a test subject who has taken the candidate anti-fatigue substance and from a test subject who has not taken the candidate anti-fatigue substance, and measuring the HHV amount in each body fluid;
(ii) a change-in-virus-amount-calculating step, which comprises calculating a change in an HHV amount in a body fluid depending on whether or not the candidate anti-fatigue substance has been taken, based on the measurement result on a change in an HHV amount depending on whether or not the candidate anti-fatigue substance has been taken, which result is obtained through the process for HHV amount-measuring step of (i), and
(iii) an anti-fatigue potency-measuring step, which comprises measuring an in vivo anti-fatigue potency of the candidate anti-fatigue substance based on the change in the amount of HHV in a body fluid depending on whether or not the candidate substance for an anti-fatigue substance has been taken, which result is obtained through the change-in-virus-amount-calculating step of (ii).

[13] The method of assessing an anti-fatigue effect of [11] or [12], wherein the method comprises assessing the anti-fatigue effect of the candidate anti-fatigue substance using the method of assessing fatigue level of any one of [1] to [8] or by using the kit for assessing fatigue level of any one of [9] to [10].

[14] The method of assessing an anti-fatigue effect of a candidate anti-fatigue substance of any one of [11] to [13], wherein the method is a method of screening for an anti-fatigue substance.

Effects of the Invention

The present invention's methods of assessing fatigue level, kits for assessing fatigue level, methods of application thereof, and methods of assessing anti-fatigue potency of anti-fatigue substances produce the effect of enabling the quantitative assessment of fatigue level of test subjects by using body fluid obtained from the subjects. Furthermore, the methods and kits of the present invention are not just simple and easy, but they also do not restrain the subjects for a long period, and therefore do not cause pain or hassle to the test subjects. The methods and such are also simple and easy for a person implementing them and are effective in that they are very easy to handle for both the test subjects and implementers. Therefore, they are very useful techniques applicable to methods of screening for anti-fatigue substances and an in vivo assessment of food products and such advertising anti-fatigue powers.

The kits for assessing fatigue level of the present invention enable the assessment of the effect and efficacy of medicines and food products having an effect of preventing or relieving fatigue, for example, by obtaining a body fluid from test subjects to determine and calculate the amount of HHV in the body fluid. In other words, an effect and efficacy of medicines or food products having a fatigue-preventing or fatigue-relieving effect within a living body can be simply, easily, and quantitatively determined.

The present invention's methods enable the simple, easy, reliable, and even quantitative measurement as to what extent an anti-fatigue substance is effective in improving human fatigue symptoms, that is, the anti-fatigue potency of the anti-fatigue substance.

The present invention provides methods and kits for simply, easily and quantitatively measuring and assessing the degree of fatigue in everyday life, as well as methods of application thereof. Thus, according to the present invention, one can objectively know the fatigue degree in everyday life and can avoid the occurrence of various diseases caused by unconsciously accumulated fatigue. Furthermore, the incidence of death from overwork, which is caused by continuing the overwork unconscious of the fatigue, can be decreased.

Furthermore, the present invention can provide consumers and society with information on the extent of the in vivo anti-fatigue potency of medicines and food products supplied abundantly in the market, which advertise fatigue-relieving effects, nutritional fortification, and nutritional support. Such information can be used as a guide for consumers to select anti-fatigue foods and medicines effective in preventing overfatigue, or those effective as nourishing tonics. In these points, the present invention is very useful and has a strong social impact.

BRIEF DESCRIPTION OF THE DRAWINGS

FIG. 1 is a schedule of the test for measuring the amount of HHV expression in Example 1.

BEST MODE FOR CARRYING OUT THE INVENTION

Figure 2:
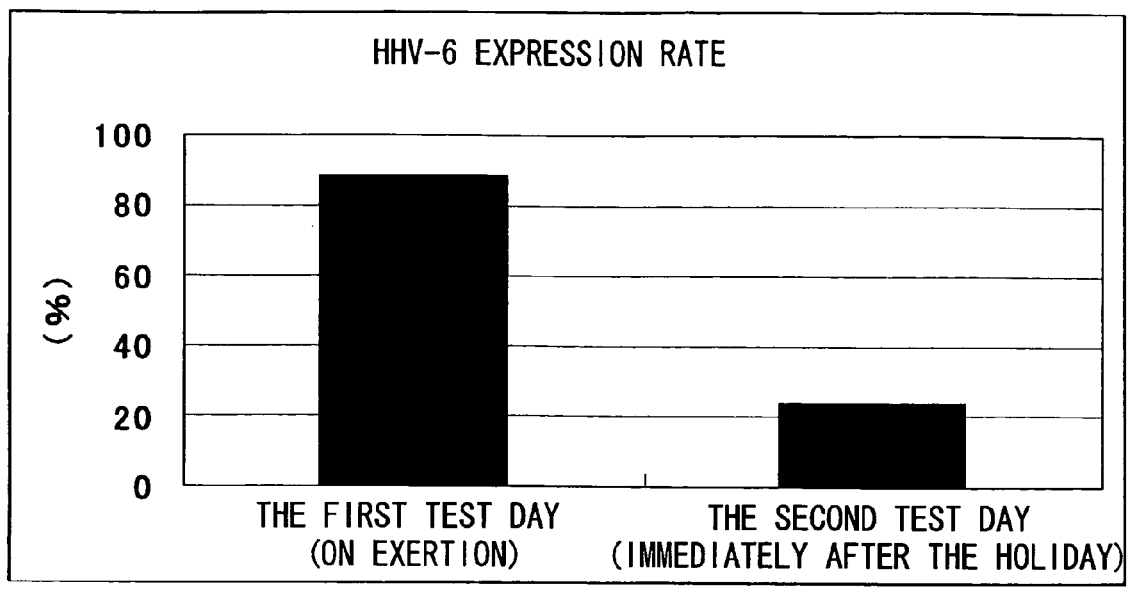
FIG. 2 depicts the measurement results of HHV expression levels in Example 1, which are displayed as a graph showing the changes in the test subjects' HHV-6 expression rate (proportion (%) of the test subjects expressing HHV-6 DNA among total test subjects). Each of the expression rates on the first test day (on exertion) and on the second test day (immediately after holiday) is shown.

Herein below, the present invention's methods and kits for assessing fatigue level and the methods of application thereof will be explained; however, the present invention is not limited thereto.

"Fatigue" in the present application refers to a tentative phenomenon observed when physical or mental burden is continuously given, and in which phenomenon, physical and/or mental functions and physical strength are qualitatively or quantitatively deteriorated. "Fatigue" is classified into physiological fatigue and pathological fatigue. "Physiological fatigue" in the present application means a tentative phenomenon observed when a healthy person is given continuous physical or mental burden, and in which phenomenon, physical and mental work capability is qualitatively or quantitatively deteriorated. "Pathological fatigue" means fatigue accompanying diseases such as chronic fatigue syndrome, mental disorders, heart disease, hepatitis, anemia, various infectious diseases, and malignant tumors.

"Physiological fatigue" is further classified into "acute fatigue" and "chronic fatigue". "Acute fatigue" in the present application means transient fatigue recoverable after a proper rest. "Chronic fatigue" means fatigue lasting for a long period of time due to the accumulation of fatigue as a result of incomplete day-to-day recovery. Medium- or long-term fatigue according to the present application means acute fatigue preceding the above-mentioned chronic fatigue.

"Acute fatigue" and "chronic fatigue" are each classified into "mental fatigue" and "physical fatigue". "Mental fatigue" in the present application means not only fatigue caused by complicated calculations and/or memorizations or by mental activities like thinking; also implied is fatigue including eyestrain and/or mental stress caused when excessive emotional activity or willpower, including patience and/or strain or frustrations arising from working under time constraints, are required. "Physical fatigue" in the present application means fatigue caused by carrying out physical work or fatigue due to effects of electromagnetic waves. Furthermore, "mental fatigue load" according to the present application means giving the above-mentioned mental fatigue.

"Prolonged (persistent) fatigue" in the present application means a state in which fatigue caused by some trigger continues for a long period of time without recovery.

"Complex fatigue" in the present application means fatigue comprising a combination of the above-mentioned various kinds of fatigue.

"Fatigue level (degree)" in the present application refers to the level/degree of a state of deterioration of physical and/or mental function and physical strength. This state is caused by the above-mentioned various "fatigues" and accompanies a unique morbid and uncomfortable feeling and a desire for resting caused by excessive physical or mental activity, or a disease. Here, "a state of deterioration of physical or mental function" means qualitative or quantitative deterioration in the capability of performing physical and mental work.

A "state of overfatigue (excess fatigue)" is a condition that leads to pathological fatigue and where biological rhythms collapse and life-maintaining functions break down as a result of continued physiological fatigue and chronic fatigue as mentioned above.

Though the present invention targets all of the above-mentioned various "fatigues", physiological fatigue, especially acute, medium- or long-term fatigue is preferred. Furthermore, in the present invention, fatigue caused by a mental fatigue load is preferred among medium- or long-term fatigues. Additionally, prolonged (persistent) fatigue and fatigue (morbid fatigue) accompanying diseases such as chronic fatigue syndrome (CFS), cancers, heart diseases, and lifestyle-related diseases are preferred as targets of the present invention.

Most appropriate virus conditions for carrying out the present invention include being a virus that has latently infected most people allowing many people be test targets, and being able to easily measure the reactivated virus.

Viruses fulfilling the above conditions include human herpesvirus (HHV). As mentioned above, three subfamilies exist in HHV; for instance, human herpesvirus 6 (HHV-6), human herpesvirus 7 (HHV-7), and human cytomegalovirus (also known as human herpesvirus 5) belong to β subfamily, and Epstein-Barr virus (EBV) belongs to γ subfamily. Among adult Japanese, 90% or more people have already been infected with the above viruses, and carry the viruses in a latent state in their bodies. Especially, HHV-6 and HHV-7 infect all people at the age of two or more and five or more, respectively; therefore all adults are considered to have latently-infected viruses in their bodies. Thus, HHV-6, HHV-7, cytomegalovirus, and Epstein-Barr virus (EBV) are considered to be suitable for the present invention.

Because the virus DNA is known to be released into saliva when these viruses are reactivated, virus reactivation can be simply and easily determined by measuring virus DNA in saliva.

Herein below, an outline of the present invention will be briefly explained. Many parts of the outline of the methods described here are common to the later-described kits and methods of application.

(1) Methods for Assessing Fatigue Level:

The present inventors discovered that human fatigue level can be simply, easily, and quantitatively measured by sampling a body fluid of test subjects to measure the amount of HHV in the body fluid. This method does not require a large apparatus and needs only a short time for obtaining a body fluid; therefore the method imposes less time constraints on the test subjects and is very simple and easy for persons implementing the method.

Although any virus belonging to human herpesvirus (HHV) family is usable as a virus targeted in the present invention, HHV-6, HHV-7, cytomegalovirus, and Epstein-Barr virus (EBV) are preferable. Furthermore, HHV-6 and HHV-7 are more preferable.

A body fluid targeted in the present invention may be at least one or more kinds of body fluids selected from blood, saliva, cerebrospinal fluid, and urine, but saliva is preferable.

Methods for collecting saliva may be at least one or more kinds selected from swabbing viscous fluid of the pharynx with a cotton bud, directly spitting out saliva into a test tube, and using a saliva-sampling tool, for example a Salivette and such. A method using a Salivette is preferable.

Treatment of the oral cavity before saliva sampling includes, for example, resting quietly without taking food for a long period of time, and rinsing out the oral cavity with water just before saliva sampling. Rinsing out the mouth with water just before saliva sampling is preferable.

Conventionally known methods can be used as a method for measuring the amount of HHV in a body fluid, and those skilled in the art can appropriately choose specific techniques and conditions. Methods for measuring the amount of a virus include those measuring the amount of viral nucleic acids and those measuring the amount of viral proteins.

As methods for measuring the amount of viral nucleic acids, included are a method that purifies DNA from saliva and measures the amount of virus DNA by a PCR method with PCR primers specific for each human herpesvirus (reference: Journal of Medical Virology, 1990, 32:139-142 "Detection of human herpesvirus 6 DNA in throat swabs by polymerase chain reaction"), a method for measuring by double-nested PCR (reference: Journal of Infectious Diseases, 1993, 167:1197-1200 "Association of HHV-6 infection of the central nervous system with recurrence of febrile convulsions"), and such. In the present invention, a double-nested PCR method or a real-time PCR method are preferable.

Methods for measuring the amount of viral protein include, for example, an immunoassay method using an antibody against a viral protein. The sandwich ELISA method is one representative example of an immunoassay (reference: J. Clin. Microbiol. 1983 May; 17 (5):942-4. "Typing of herpes simplex virus isolates by enzyme-linked immunosorbent assay: comparison between indirect and double-antibody sandwich techniques." Gema G. Battaglia M, Revello M C, Gema M T.)

In the present invention's methods for measuring fatigue level, it is preferable to assess a fatigue level of a subject to be high when the above-mentioned HHV amount in a body fluid is high. This is because that the amount of HHV expression in a body fluid of test subjects increases as the subject's fatigue degree rises, as shown in the Examples described later.

Furthermore, it is obvious for those skilled in the art that a part or all of the methods for assessing fatigue level according to the present invention can be practiced by using a conventionally known calculating apparatus (a data-processing apparatus) such as a computer. For example, the methods for assessing fatigue degree according to the present invention can be said to comprise a measurement process in which the amount of HHV in a body fluid is measured and an assessment process in which fatigue level of a subject is assessed based on the measurement results of HHV amount in the body fluid. Among these processes, a calculating apparatus is especially utilizable in the assessment process.

(2) Kits for Assessing Fatigue Level:

Next, the present invention's kits for assessing fatigue level will be explained. The kits for assessing fatigue level according to the present invention are for assessing fatigue level in humans. In other words, any kits for carrying out the present invention's methods for assessing fatigue level as explained in the above section (1) are included. In more detail, the kits can be those comprising a means for measuring the amount of HHV in a body fluid of test subjects. As a means for measuring the amount of HHV in a body fluid according to the present invention, any means necessary to practice conventionally known measurement methods can be used. Specifically, a means necessary to practice conventionally known measurement methods includes, for example, reagents, apparatuses, equipments, catalysts, and such that are necessary to carry out the methods for measuring the amount of HHV in a body fluid as explained in the above section (1). The kits for assessing fatigue degree according to the present invention may comprise a means for obtaining body fluid of test subjects. Labels on the packaging material of the kits or documents attached to them may indicate that the kits can be used to assess fatigue level of test subjects by using human herpesvirus (HHV) amount in a body fluid as an indicator.

Furthermore, the kits for assessing the degree of fatigue according to the present invention may be kits comprising a conventionally known calculating apparatus such as a computer.

(3) Applications of the Methods and Kits for Assessing Fatigue:

As mentioned above, the methods and kits for assessing fatigue level according to the present invention enable the quantitative measurement and assessment of the anti-fatigue potency of an anti-fatigue substance in the body of a test subject by measuring the amount of HHV in a body fluid of the test subject before and after the test subject takes the anti-fatigue substance. Furthermore, such methods and kits are both simple and easy, and also do not require a large apparatus or long time constraints; therefore they are advantageous in being easy in handling for both test subjects and operators.

Therefore, the present invention also includes methods for measuring the anti-fatigue potency of an anti-fatigue substance by using either the methods or kits for assessing fatigue level according to the present invention. Such methods for measuring the anti-fatigue potency of an anti-fatigue substance can be said to comprise, for example, the following processes:

(i) a pre-intake HHV amount-measuring step, which comprises obtaining a body fluid from a test subject before the test subject takes the candidate anti-fatigue substance and measuring the amount of HHV in the body fluid;

(ii) a post-intake HHV amount-measuring step, which comprises obtaining a body fluid from the test subject after the test subject takes the candidate anti-fatigue substance and measuring the amount of HHV in the body fluid;

(iii) a change-in-virus-amount-calculating step, which comprises calculating a change in an HHV amount in a body fluid before and after the intake of the candidate anti-fatigue substance, based on the measurement result on a change in an HHV amount before and after the intake of the candidate anti-fatigue substance, which result is obtained through the pre-intake HHV amount-measuring step of (i) and the post-intake HHV amount-measuring step of (ii); and (iv) an anti-fatigue potency-measuring step, which comprises measuring an in vivo anti-fatigue potency of the candidate anti-fatigue substance based on the change in the HHV amount in the body fluid before and after the intake of the candidate anti-fatigue substance, which change is obtained by the change-in-virus-amount-calculating step of (iii).

Furthermore, the present invention's methods for measuring the anti-fatigue potency of a candidate substance for an anti-fatigue substance (hereafter "candidate anti-fatigue substance") can be carried out as methods in which the above-mentioned methods for measuring anti-fatigue potency is applied to test subjects administered with the candidate substance for an anti-fatigue substance (administered group), and to test subjects not administered with the substance (non-administered group).

One of ordinary skill in the art can appropriately choose the method of intake by which test subjects take the candidate anti-fatigue substance. "Intaking" in the present application means not only the test subject's ingestion of the substance as a food and drink, but also the oral or parenteral administration of the substance.

Being "anti-fatigue" according to the present application means having an effect of relieving, suppressing, or preventing fatigue. "Anti-fatigue substances" include substances having the effect to relieve, suppress, or prevent fatigue, and substances supplementing biological functions. "Substances supplementing biological functions" mean substances that adjust the balance in the body and comprise substances or such that have a function of enhancing an immune function.

The present invention's methods and kits for assessing fatigue level are applicable, for example, to methods of screening for an anti-fatigue substance. In other words, methods of screening for an anti-fatigue substance according to the present invention can be any method as long as it utilizes either an above-mentioned method for assessing anti-fatigue level or a kit for assessing anti-fatigue level to screen for an anti-fatigue substance, and the specific methods and conditions are not restricted.

The above-mentioned screening methods enable simple, easy, and objective selection of food products that actually show a good anti-fatigue activity in vivo, for example, by orally administering to test subjects a food product that is likely to be applicable as an anti-fatigue food. Therefore, an anti-fatigue substance or anti-fatigue food selected by the above-mentioned screening methods has a proved in vivo effect and will be able to obtain a high appraisal in the market.

Novel anti-fatigue substances according to the present invention can be any substance obtained by the above screening methods, and anti-fatigue substances obtained by the above screening methods are also included in the present invention.

As fatigue turned into a social problem, the types and amounts of anti-fatigue substances and anti-fatigue food products advertising anti-fatigue functions have increased, strongly requiring the development of a method for appropriately assessing their anti-fatigue potency. These needs can be addressed by utilizing the present invention's methods and kits for assessing fatigue level and their methods of application.

Herein below, modes for carrying out the present invention will be explained in more detail by using examples based on the attached drawings. Needless to say, the present invention is not restricted to the following examples, and details can obviously include variations. Furthermore, the present invention is not restricted to the above-mentioned embodiments. Various modifications are possible, and embodiments obtainable by appropriately combining each disclosed technical means are also comprised within the technical scope of the present invention.

The present invention is a product of the research project "Molecular/neural mechanisms of fatigue and fatigue sensation and the development of the way to overcome fatigue", in "Studies corresponding to needs of people" funded through the Special Coordination Funds for Promoting Science and Technology of the Ministry of Education, Culture, Sports, Science and Technology (MEXT), Japan.

All prior art references cited herein are incorporated by reference.

EXAMPLE 1

Targeting healthy individuals, the expression of HHV-6 DNA in saliva of test subjects during work and before and after rest was measured. The number of target test subjects was 20 (eleven males and nine females), and the average age was 34.45±8.92. The present Example was conducted using samples obtained from the test subjects participating in the present study, after fulfilling informed consent conditions.

(1) Measurement of Fatigue Level (1-1) Test Schedule

Saliva sampling from test subjects was carried out according to the test schedule shown in FIG. 1. During the resting period, the test subjects did not do any work, and avoided excessive exercise.

(1-2) Method of Saliva Sampling

Test subjects were fasted from nine in the evening of the day prior to the test day. The test subjects rinsed the oral cavity twice with distilled water just before saliva sampling, which was done by holding inner cotton of a Salivette (SARSTEDT AG & Co.) in the oral cavity for two minutes.

(1-3) Method for Sample Preservation

Sampled saliva was preserved by freezing (−80° C.) on the same day.

(1-4) Purification of DNA

Purification of DNA from the collected saliva samples was carried out in the presence of carrier RNA using a commercially available kit for DNA purification (QIAamp MinElute Virus Spin Kit, QIAGEN).

(1-5) Measurement of the Amount of Viral DNA of HHV

The measurement of the amount of herpesvirus DNA was carried out by using a double-nested PCR method with PCR primers specific for each of the four species HHV-6, HIV-7, human cytomegalovirus, and Epstein-Barr virus (EBV). Among HHV-6-specific PCR primer sequences, the sequences of the first PCR primer are shown in SEQ ID NOs: 1 and 2, and the sequences of the second PCR primer are shown in SEQ ID NOs: 3 and 4. Among HHV-7-specific PCR primer sequences, the sequences of the first PCR primer are shown in SEQ ID NOs: 5 and 6, and the sequences of the second PCR primer are shown in SEQ ID NOs: 7 and 8. Among human cytomegalovirus-specific PCR primer sequences, the sequences of the first PCR primer are shown in SEQ ID NOs: 9 and 10, and the sequences of the second PCR primers are shown in SEQ ID NOs: 11 and 12. Among Epstein-Barr virus (EBV)-specific PCR primer sequences, the sequences of the first and the second PCR primers are shown in SEQ ID NOs: 13 and 14. The same primer sequences were used in the first and the second PCR for Epstein-Barr virus (EBV).

A Reference for the Measurement of the Amount of HHV-6 DNA:

Journal of Virol. 2002, 76(8): 4145-4151, K. Kondo et al. "Identification of human herpesvirus 6 latency-associated transcripts."

A Reference for the Measurement of the Amount of Human Cytomegalovirus DNA:

Proc. Natl. Acad. Sci. USA 1996, 93: 11137-11142, K. Kondo et al. "Human cytomegalovirus latent gene expression in granulocyte-macrophage progenitors in culture and in healthy seropositive individuals."

(2) Results

Among the above four species of viruses, HHV-6 and HHV-7 were found to be frequently detected in saliva of healthy adults. On the other hand, the detection frequency for human cytomegalovirus and Epstein-Barr virus was lower than that for HHV-6 and HHV-7.

The measurement results on the amount of HHV-6 DNA are shown in FIG. 2. For one measurement, 20 μl saliva was used. HHV-6 DNA was detected in 88% of the test subjects engaged in moderately excessive work due to prolonged working time and such (the first test day). In contrast, HHV-6 DNA was detected in 23.8% of the test subjects immediately after a holiday (the second test day). These results show that HHV-6 is significantly reactivated on exertion. These results led to the discovery that HHV-6 DNA expressed in saliva through the reactivation of HHV-6 is a fatigue biomarker (a biological index factor) that varies according to fatigue. Accordingly, an objective method for assessing fatigue degree by detecting HHV-6 DNA released into saliva as a result of the reactivation of HHV-6 was developed, enabling a simple and easy assessment of fatigue degree.

EXAMPLE 2

(3) The Amount of HHV-7 Expression in Chronic Fatigue Syndrome (CFS) Patients (3-1) Testing Methods Twenty-four chronic fatigue syndrome (CFS) patients and the twenty healthy individuals of Example 1 were targeted. As the patients, CFS patients attending the CFS outpatient unit of Osaka University Hospital who fulfilled the diagnostic criteria of the Ministry of Health, Labour and Welfare were targeted. The present Example was conducted using samples obtained from the test subjects participating in the present study, after fulfilling informed consent conditions.

(3-2) Method of Saliva Sampling

Subjects rinsed the oral cavity twice with distilled water just before saliva sampling, which was done by holding inner cotton of a Salivette (SARSTEDT AG & Co.) in the mouth cavity for two minutes.

(3-3) Method of Detection

The detection and measurement of HHV were done in the same manner as in items (1-3) and (1-5) of Example 1.

(4) Results

Among the above-mentioned four species of viruses, HHV-7 was especially found to be frequently and abundantly detected in saliva of patients. On the other hand, the detection frequency of human cytomegalovirus, HHV-6, and Epstein-Barr virus was lower compared to that of HHV-7.

Figure 3:
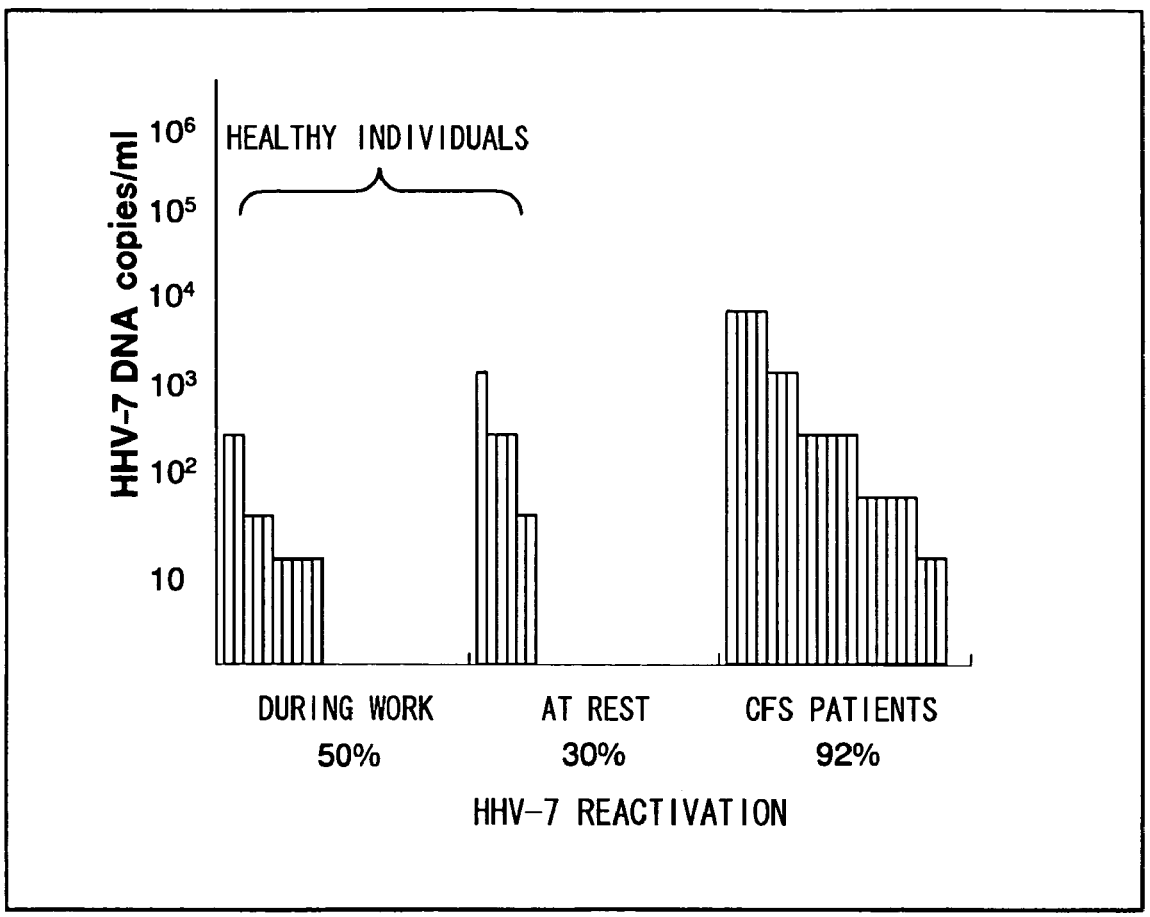
FIG. 3 depicts the results of measurement of the amounts and frequency of HHV DNA expression in Example 2, which are displayed as a graph showing the changes in the amount and frequencies of HHV-7 DNA expression in CFS patients and healthy individuals. The vertical axis shows the expressed amount of HHV-7 DNA, and each column shows individual test subjects for whom positive expression was observed.

The measurement results of HHV-7 are shown in FIG. 3. The amount of HHV-7 DNA was semi-quantitatively measured by conducting a double-nested PCR method after serially diluting 20 μl of saliva. HHV-7 DNA was detected in 92% of CFS patients among the test subjects. In contrast, in healthy individuals, HHV-7 DNA was detected in 50% of test subjects during work and in only 30% of test subjects at rest. The amount of HHV-7 DNA in half of the CFS patients reached an amount 10 to 100 fold larger than the average amount detected in healthy persons. These results show that HHV-7 is significantly reactivated in the chronic fatigue state that accompanies disease. These results led to the discovery that HHV-7 DNA expressed in saliva due to reactivation of HHV-7 is a fatigue biomarker (a biological index) that varies according to chronic fatigue caused by diseases or such. Accordingly, an objective method for assessing the degree of fatigue by detecting HHV-7 DNA released into saliva due to reactivation of HHV-7 was developed, enabling simple and easy assessment of decline in physical strength caused by chronic fatigue.

INDUSTRIAL APPLICABILITY

The methods for assessing fatigue level according to the present invention can be used to elucidate mechanisms of stress and/or fatigue. The methods can also be used to develop stress-relieving methods, to assess the extent of fatigue, and to assess the decline in physical strength that accompanies a disease. By applying the present invention, it is possible to quantify (assess) the effect of health foods, foods for specified health uses, nutrition-supplement drinks, and substances supplementing biological functions in the market that advertise anti-fatigue activity. Accordingly, the present invention is applicable to a broad range of fields such as medical services, drug manufacturing, health food industry, health equipment industry, and such.

The invention claimed is:

1. A method of assessing if a test subject is in a state of physiological fatigue comprising:
   (a) preparing a saliva sample from a test subject;
   (b) measuring the amount of human herpesvirus 6 or 7 viruses in the saliva sample by measuring the amount of human herpesvirus 6 or 7 DNA present in the sample by polymerase chain reaction (PCR); and
   (c) determining if the amount of either human herpesvirus 6 or 7 in the saliva sample is higher than the average amount detected in healthy persons whose physical and mental work capability is not deteriorated,
      wherein a higher than average amount of either human herpesvirus 6 or 7 in saliva signifies that the test subject is experiencing a reactivated human herpsevirus 6 or 7 viral infection and
      wherein the higher than average amount of either human herpesvirus 6 or 7 in saliva is a positive indication of physiological fatigue.

2. The method of claim 1, wherein the test subject is in a state of fatigue due to an accumulation of physiological fatigue arising from everyday life.

3. The method of claim 1, wherein said PCR is double-nested PCR or real-time PCR.

4. A method of assessing if a test subject is in a state of physiological fatigue comprising:
   (a) preparing saliva samples from healthy adults immediately after resting period;
   (b) preparing a saliva sample from the test subject at an arbitrary time point;
   (c) measuring the amount of human herpesvirus 6 or 7 in the sample obtained in (a) and (b) by polymerase chain reaction (PCR); and
   (d) assessing that the test subject is in a state of physiological fatigue when the amount of human herpesvirus 6 or 7 in the sample obtained in (b) is greater than the average amount of human herpesvirus 6 or 7 in the sample obtained in (a).

5. A method of assessing the physiological fatigue level of a test subject comprising:
   (a) preparing saliva samples from a test subject immediately after resting period;
   (b) preparing a saliva sample from the test subject of (a) at an arbitrary time point;
   (c) measuring the amount of human herpesvirus 6 or 7 in the sample obtained in (a) and (b) by polymerase chain reaction (PCR); and
   (d) assessing that the physiological fatigue level of the test subject is high when the amount of human herpesvirus 6 or 7 in the sample obtained in (b) is greater than the average amount of human herpesvirus 6 or 7 in the sample obtained in (a).

6. A method of assessing the increase or decrease in the physiological fatigue level of a test subject comprising:
   (a) preparing a base line saliva sample from a test subject;
   (b) preparing a saliva sample from a test subject of (a) at a time point different from when the base line sample of (a) is obtained;
   (c) measuring the amount of human herpesvirus 6 or 7 in the samples obtained in (a) and (b) by polymerase chain reaction (PCR); and
   (d) assessing that the physiological fatigue level of the test subject at the time point,
      wherein if the amount of human herpesvirus 6 or 7 in the sample obtained in (b) is significantly greater than the amount of human herpesvirus 6 or 7 in the sample obtained in (a), then the physiological fatigue level is increased and
      wherein if the amount of human herpesvirus 6 or 7 in the sample obtained in (b) is significantly less than the amount of human herpesvirus 6 or 7 in the sample obtained in (a), then the physiological fatigue level is decreased.

7. A method of assessing the physiological fatigue level of a test subject comprising:
   (a) preparing a saliva sample from a healthy adult immediately after resting period;
   (b) preparing a saliva sample from the test subject at an arbitrary time point;
   (c) measuring the amount of human herpesvirus 6 or 7 in the samples obtained in (a) and (b) by polymerase chain reaction (PCR); and
   (d) assessing that the physiological fatigue level of the test subject is higher than the physiological fatigue level of the healthy adult immediately after resting period when the amount of human herpesvirus 6 or 7 in the sample obtained in (b) is significantly greater than the amount of human herpesvirus 6 or 7 in the sample obtained in (a).

8. A method of assessing the physiological fatigue level of a test subject comprising:
   (a) preparing a saliva sample from a test subject immediately after resting period;
   (b) preparing a saliva sample from the test subject at an arbitrary time point;
   (c) measuring the amount of human herpesvirus 6 or 7 in the samples obtained in (a) and (b) by polymerase chain reaction (PCR); and
   (d) assessing that the physiological fatigue level of the test subject at the time point when the sample obtained in (b) at an arbitrary time point is higher than the physiological fatigue level of the test subject immediately after resting period when the amount of human herpesvirus 6 or 7 in the sample obtained in (b) is significantly greater than the amount of human herpesvirus 6 or 7 in the sample obtained in (a).

* * * * *